(12) United States Patent
Marshall (10) Patent No.: US 10,092,669 B2
(45) Date of Patent: Oct. 9, 2018

(54) STERILIZING RADIATION SYSTEM FOR USE WITH DOOR HANDLE

(71) Applicant: STRATEGIC PARTNERSHIPS ALLIANCE, LLC, Grass Valley, CA (US)

(72) Inventor: John J. Marshall, Beverly Hills, CA (US)

(73) Assignee: STRATEGIC PARTNERSHIPS ALLIANCE, LLC, Grass Valley, CA (US)

( * ) Notice: Subject to any disclaimer, the term of this patent is extended or adjusted under 35 U.S.C. 154(b) by 0 days.

(21) Appl. No.: 15/597,996

(22) Filed: May 17, 2017

(65) Prior Publication Data

US 2017/0246332 A1    Aug. 31, 2017

Related U.S. Application Data

(63) Continuation-in-part of application No. 13/966,563, filed on Aug. 14, 2013.

(60) Provisional application No. 61/683,002, filed on Aug. 14, 2012.

(51) Int. Cl.
| | | |
|---|---|---|
| *G01N 23/00* | (2006.01) | |
| *A61L 2/24* | (2006.01) | |
| *A61L 2/10* | (2006.01) | |
| *A61L 2/08* | (2006.01) | |

(52) U.S. Cl.
CPC .............. *A61L 2/24* (2013.01); *A61L 2/085* (2013.01); *A61L 2/10* (2013.01); *A61L 2202/11* (2013.01); *A61L 2202/14* (2013.01); *A61L 2202/20* (2013.01)

(58) Field of Classification Search
CPC .................................................. A61L 2/0029
USPC ... 250/453.11, 454.11, 455.11, 492.1, 492.3, 250/493.1
See application file for complete search history.

(56) References Cited

U.S. PATENT DOCUMENTS

| | | |
|---|---|---|
| 4,896,042 A | 1/1990 | Humphreys |
| 4,952,369 A | 8/1990 | Belilos |
| 5,039,865 A | 8/1991 | Koji |
| 5,788,364 A | 8/1998 | Cooper et al. |
| 5,816,692 A | 10/1998 | Cooper et al. |
| 5,920,075 A | 7/1999 | Whitehead |
| 5,997,154 A | 12/1999 | Cooper et al. |
| 6,110,424 A | 8/2000 | Maiden et al. |
| 6,361,194 B1 | 3/2002 | Evans et al. |
| 6,461,568 B1 | 10/2002 | Eckhardt |
| 6,579,495 B1 | 1/2003 | Maiden |
| 6,585,392 B2 | 7/2003 | Shiau et al. |
| 6,688,763 B2 | 2/2004 | Pameijer et al. |
| 7,989,779 B1 * | 8/2011 | Ray ............. A61L 2/10 250/455.11 |
| 2003/0231993 A1 | 12/2003 | Yan |
| 2004/0155201 A1 | 8/2004 | Russell et al. |
| 2006/0134713 A1 | 6/2006 | Rylatt et al. |

(Continued)

*Primary Examiner* — Jason McCormack
(74) *Attorney, Agent, or Firm* — Brunda Garred & Brucker (57) ABSTRACT

A sterilization system is configured to emit energy, such as UV radiation, for sterilizing a surface, such as a door handle, faucet handle, elevator button, or other target surfaces known in the art. The sterilization system is configured to operate automatically in response to detection of a user's hand interfacing with the handle. After a user releases a handle, the sterilization system is actuated to sanitize the handle for subsequent users.

5 Claims, 7 Drawing Sheets

(56) References Cited

U.S. PATENT DOCUMENTS

| | | |
|---|---|---|
| 2007/0145292 A1 | 6/2007 | Jones |
| 2008/0187190 A1 | 8/2008 | Shin et al. |
| 2008/0265179 A1 | 10/2008 | Havens et al. |
| 2011/0174992 A1 | 7/2011 | Sakita |
| 2012/0305804 A1* | 12/2012 | Goldman .............. E05B 1/0069 250/492.1 |
| 2013/0256560 A1* | 10/2013 | Yerby ....................... A61L 2/10 250/455.11 |

* cited by examiner

STERILIZING RADIATION SYSTEM FOR USE WITH DOOR HANDLE

CROSS-REFERENCE TO RELATED APPLICATIONS

The present application is a continuation-in-part of U.S. patent application Ser. No. 13/966,563, entitled STERILIZATION SYSTEM USING ULTRAVIOLET AND INFRARED RAYS, filed Aug. 14, 2013, which claims benefit of U.S. Provisional Application Ser. No. 61/683,002, filed Aug. 14, 2012, the contents of each of which are expressly incorporated herein by reference.

STATEMENT RE: FEDERALLY SPONSORED RESEARCH/DEVELOPMENT

Not Applicable

BACKGROUND

Field of Invention

This invention relates in general to a sterilization system, and more specifically, to a sterilization system which utilizes optical energy, e.g., light, for killing germs and bacteria on a door handle or other surfaces routinely grabbed or manually actuated, particularly in public locations.

Description

The transfer of germs, bacteria and viruses and other contaminants is well-known to lead to the development of a cold or other disease/illness. Such transfer is particularly prevalent in public areas, where several individuals interact with each other and the surrounding environment. For instance, manually actuated devices, such as door handles, faucet handles, elevator buttons, and the like tend to be common areas for transfer of such contaminants, as they are regularly engaged by several individuals during the course of a given day.

Such health concerns are well-known, and typically combated through routine cleaning. For instance, a cleaning staff typically cleans such areas on a regular basis, which may be daily or even more frequent. The contaminants may be killed or removed through the use of cleaning agents/detergents, wherein such cleaning agents may be sprayed or wiped on the surface of the door handle, etc.

Although the practice of using cleaning agents is helpful in trying to maintain a clean, sanitary environment, there are several deficiencies associated with such practice. One deficiency is that it is difficult to maintain sanitary conditions for extended periods of time. For instance, if a cleaning staff is scheduled to clean an area once a day, several contaminants may build-up on the surfaces of the handles, etc., throughout the day and may be transferred to people who interface with those handles while the contaminants are present. In this regard, there are logistical and cost issues associated with continually maintaining public areas in a sanitary condition.

Another deficiency is associated with the cleaning agents used by the cleaning staff. More specifically, such cleaning agents may be toxic to one's health and may cause harm to the environment.

Yet another shortcoming associated with conventional sterilization practices is that several areas may be overlooked for sterilization. It is difficult to sanitize every handle, or every elevator button, etc. within a building on a routine basis.

As such, there is a need in the art for an improved sterilization system which is configured to maintain more sanitary conditions in more cost effective and environmentally friendly conditions. The present invention address this particular need, as will be discussed in more detail below.

BRIEF SUMMARY

According to an aspect of the present invention, there is provided a sterilization system configured to emit optical energy, e.g., light, for sterilizing a surface, such as a door handle, faucet handle, elevator button, or other target surfaces known in the art. The sterilization system is configured to operate automatically in response to detection of a user's hand interfacing with the handle. In other words, after a user releases a handle, the sterilization system is actuated to sanitize the handle for subsequent users.

According to one embodiment, there is provided a sterilization system configured for use with a door having a user actuated opening mechanism (such as a handle). The sterilization system includes a motion sensor configured to detect placement and removal of a hand of a user adjacent the opening mechanism. A controller is in communication with the motion sensor, and is configured to generate a sterilization cycle command in response to detection, by the motion sensor, of placement and removal of the hand of the user adjacent the opening mechanism. A first sanitizing light element is in communication with the controller for receiving the sterilization cycle command and is positionable in optical range of the opening mechanism. The first sanitizing light element is sized, configured and adapted to emit a first optical sterilization signal toward the opening mechanism for sterilizing the opening mechanism in response to receipt of sterilization cycle command. To that end, it is contemplated that the first sanitizing light element will extend perpendicularly outward from the door and oriented downward toward the handle a distance from one to three inches, with two to three inches being preferred.

A second sanitizing light element may be in communication with the controller for receiving the sterilization cycle command and may be positionable in spaced relation to the first sanitizing light element and in optical range of the opening mechanism. The second sanitizing light element may be sized, configured and adapted to emit a second optical sterilization signal toward the opening mechanism. The second sanitizing light will be oriented such that the same will extend perpendicularly outward from the door a distance of at least three inches to thus enable the sanitizing light to more broadly project upwardly upon the surfaces to be sterilized. The first and second optical sterilization signals may thus collectively sterilize the opening mechanism in response to receipt of sterilization cycle command.

The sterilization system may include a housing assembly coupled to the first sanitizing light element and include a shield and a chassis coupled to the shield. The first sanitizing light element may be coupled to the chassis, and the shield may be configured to block light emitted away from the opening mechanism.

The first sanitizing light element may be configured to emit ultraviolet light, such as C-spectrum ultraviolet light. The first sanitizing light element may also be configured to emit infrared light. The first sanitizing light element may be configured to emit light at a wavelength of approximately 240-270 nanometers, with 253.7 nm being preferred.

The controller may be configured to generate a stop command in response to detection of placement of the hand of the user adjacent the opening mechanism during emission of light by the first sanitizing light element. The first sanitizing light element may be configured to stop emitting light in response to receipt of the stop command.

The motion sensor may be configured to detect placement and removal of the hand of the user within approximately 5 inches of the opening mechanism.

The present invention is best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which.

Common reference numerals are used throughout the drawings and detailed description to indicate like elements.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

According to various aspects of the present invention, and referring now to the drawings, there is provided a sterilization system 10 configured to emit optical energy, e.g., light, for sterilizing a door handle 12. One or more sanitizing light elements 14 are mounted in close proximity to the handle 12 for emitting light at a sanitizing light frequency to kill bacteria, viruses or other contaminants which may be present on the door handle 12. The sterilization system 10 may be configured to detect the presence of the user's hand grabbing the handle 12, and automatically initiate a sterilization cycle in response to the user releasing the handle 12.

Figure 1:
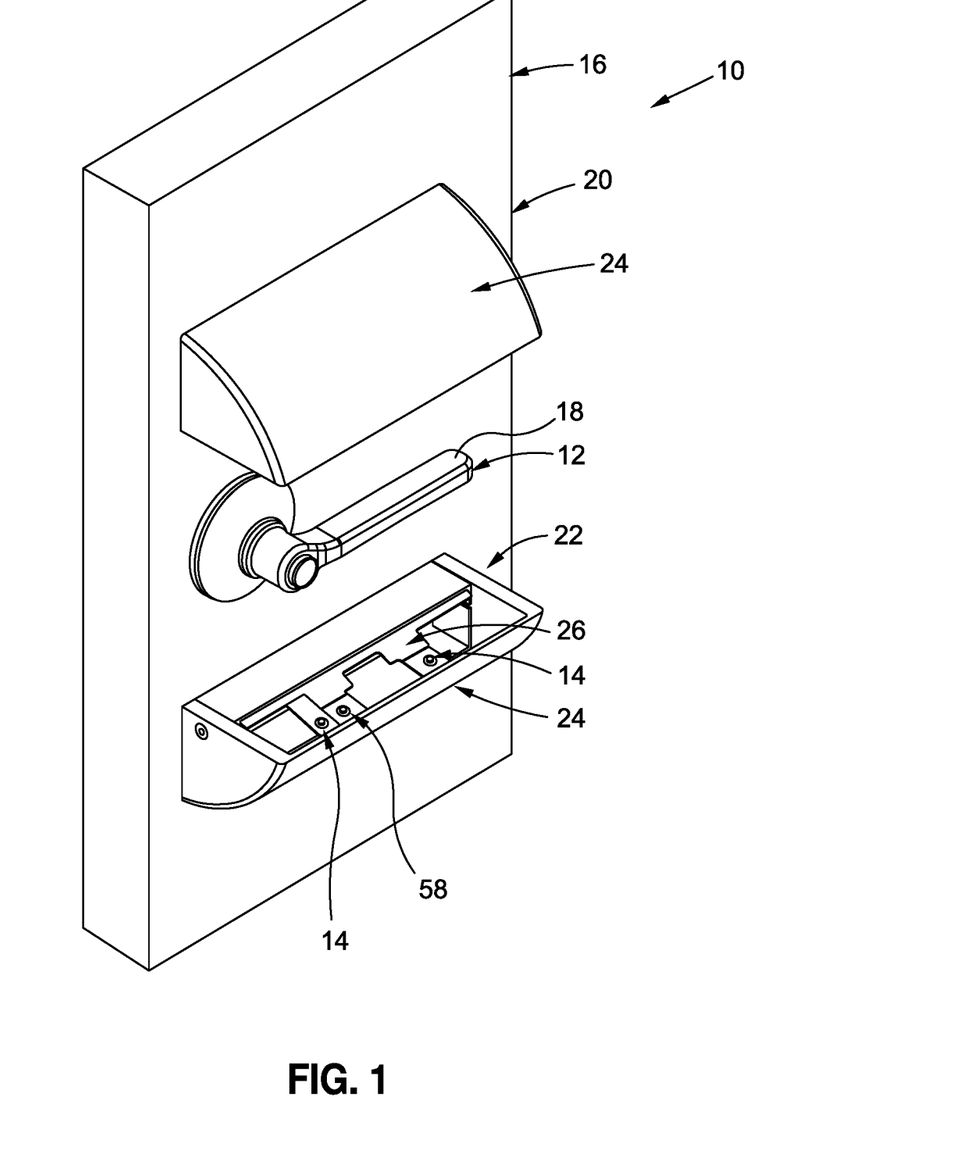
FIG. 1 is an upper perspective view of door having a sterilization system constructed in accordance with an embodiment of the present invention coupled thereto.
Figure 2:
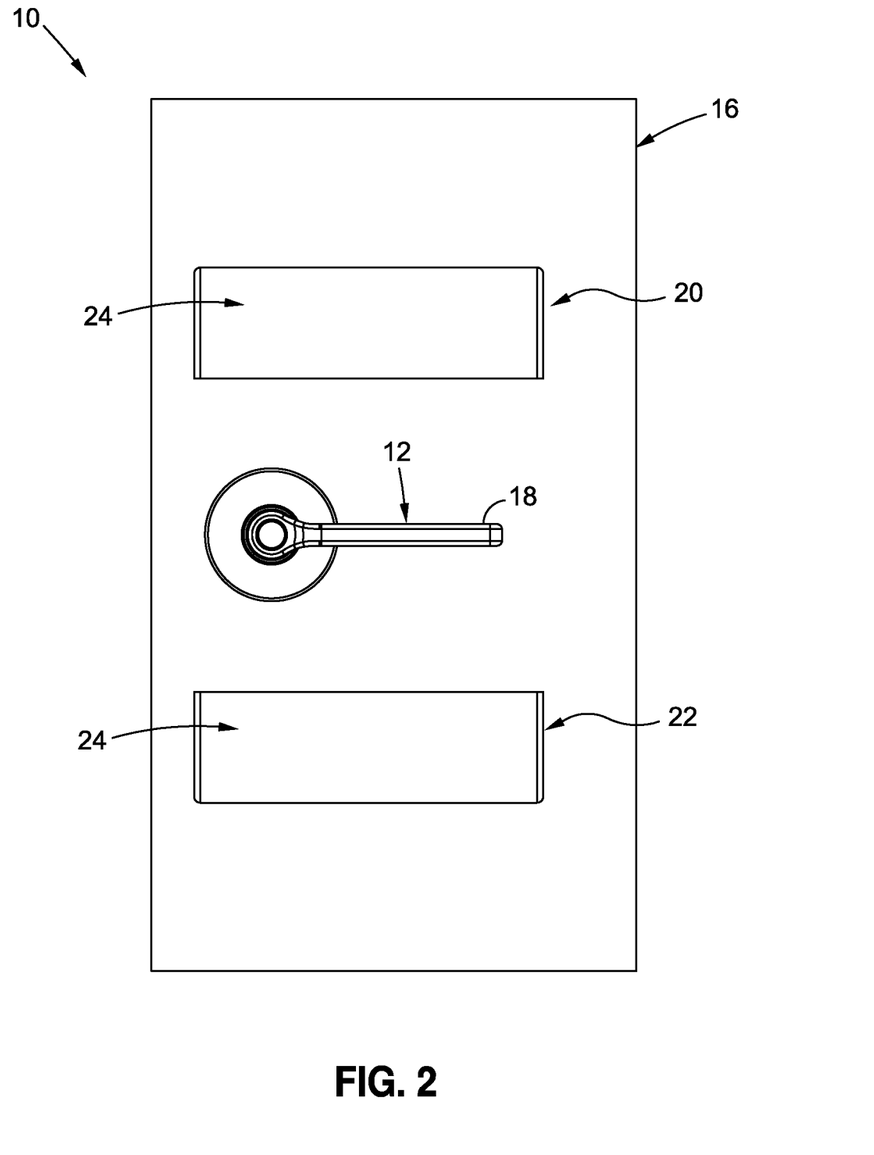
FIG. 2 is a front view of the door depicted in FIG. 1.
Figure 3:
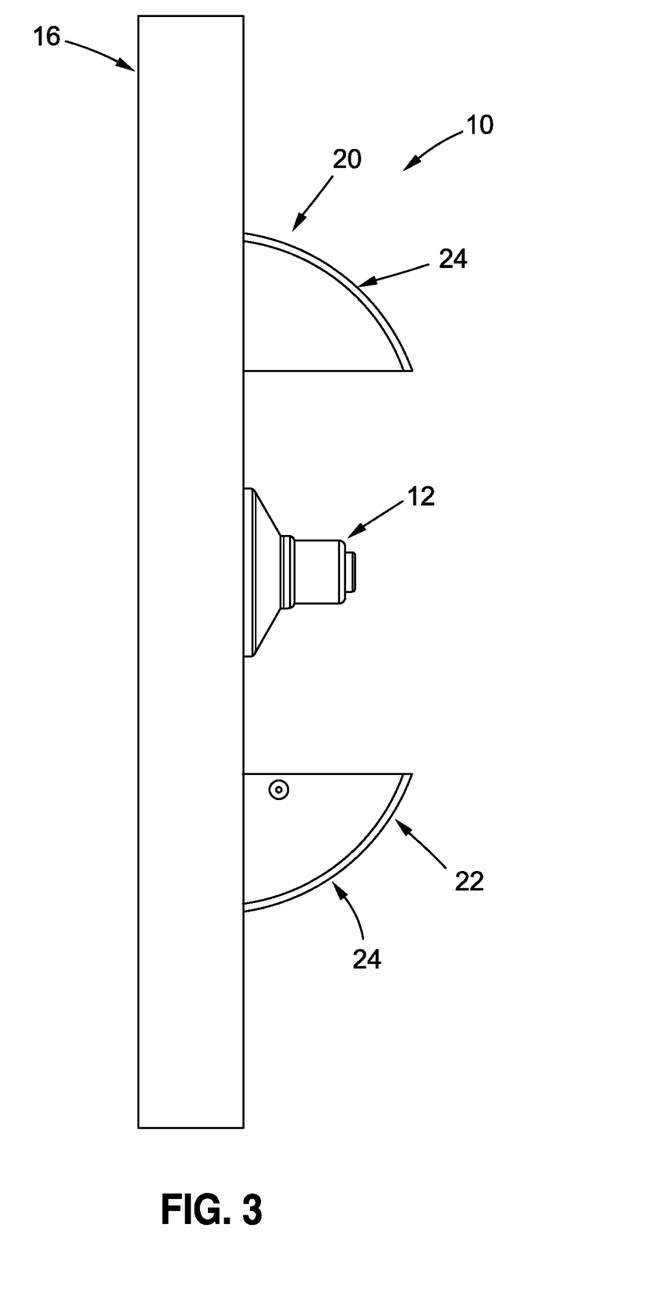
FIG. 3 is a side view of the door depicted in FIG. 1.

According to one embodiment, the sterilization system 10 is configured for use with a door 16 having a user actuated opening mechanism 12 including a gripping surface/target surface 18 which is interface with a user for opening the door 16. As used herein the term "opening mechanism" may refer to a door handle, a faucet handle, an elevator button, a biometric security device, a keypad/keyboard, or other handles, buttons or other grippable/engageable elements known by those skilled in the art. In the exemplary embodiment depicted in FIG. 1, the opening mechanism 12 includes a rotatable handle having an elongate gripping portion defining a target/gripping surface 18 which is grabbed by the user to actuate the handle 12.

The exemplary sterilization system 10 includes a first, upper sterilization assembly 20 coupled to the door 16 and positioned above the handle 12, and a second, lower sterilization assembly 22 coupled to the door 16 and positioned blow the handle 12. Each sterilization assembly includes a shield 24, a chassis 26, and at least one sanitizing light element 14 for emitting light at a sanitizing wavelength. The sterilization assemblies 20, 22 are coupled to the door 16 in close proximity to the handle 12 such that the sanitizing light elements 14 are in effective range of the handle 12. Typically, the sanitizing light elements 14 are positioned approximately one to five inches away (i.e., above or below) from the handle 12, which provides suitable space for a user to grab the handle 12 and actuate the handle 12. In a most highly preferred embodiment, discussed more fully below, the lower sterilization assembly 22 will extend outwardly from door 16 a length greater than upper sterilization assembly 20 to thus enable the sanitizing light assembly disposed therein to have a greater projection of sanitizing light relative the sanitizing light element 14 disposed within upper sanitizing light assembly 20. However, in other embodiments, the sanitizing light elements 14 may be positioned closer to the handle 12 or farther away from the handle 12 without departing from the spirit and scope of the present invention.

Each sanitizing light element 14 is preferably comprised of a light emitting diode (LED) configured to emit light at a sterilizing wavelength. As used herein, the term "sterilizing wavelength" refers to any wavelength which can kill, neutralize or otherwise remove a contaminant, such as bacteria, viruses, germs or other contaminants known in the art. According to one embodiment, the sterilizing wavelength is in the range of approximately 240 to 270 nanometers, with 253.7 nm being most highly preferred, although other wavelengths known in the art may also be used. The sanitizing light elements 14 may be configured to emit ultraviolet light, preferably in the C-spectrum, or infrared light, although those skilled in the art will recognize that other types of light may also be emitted.

Figure 6:
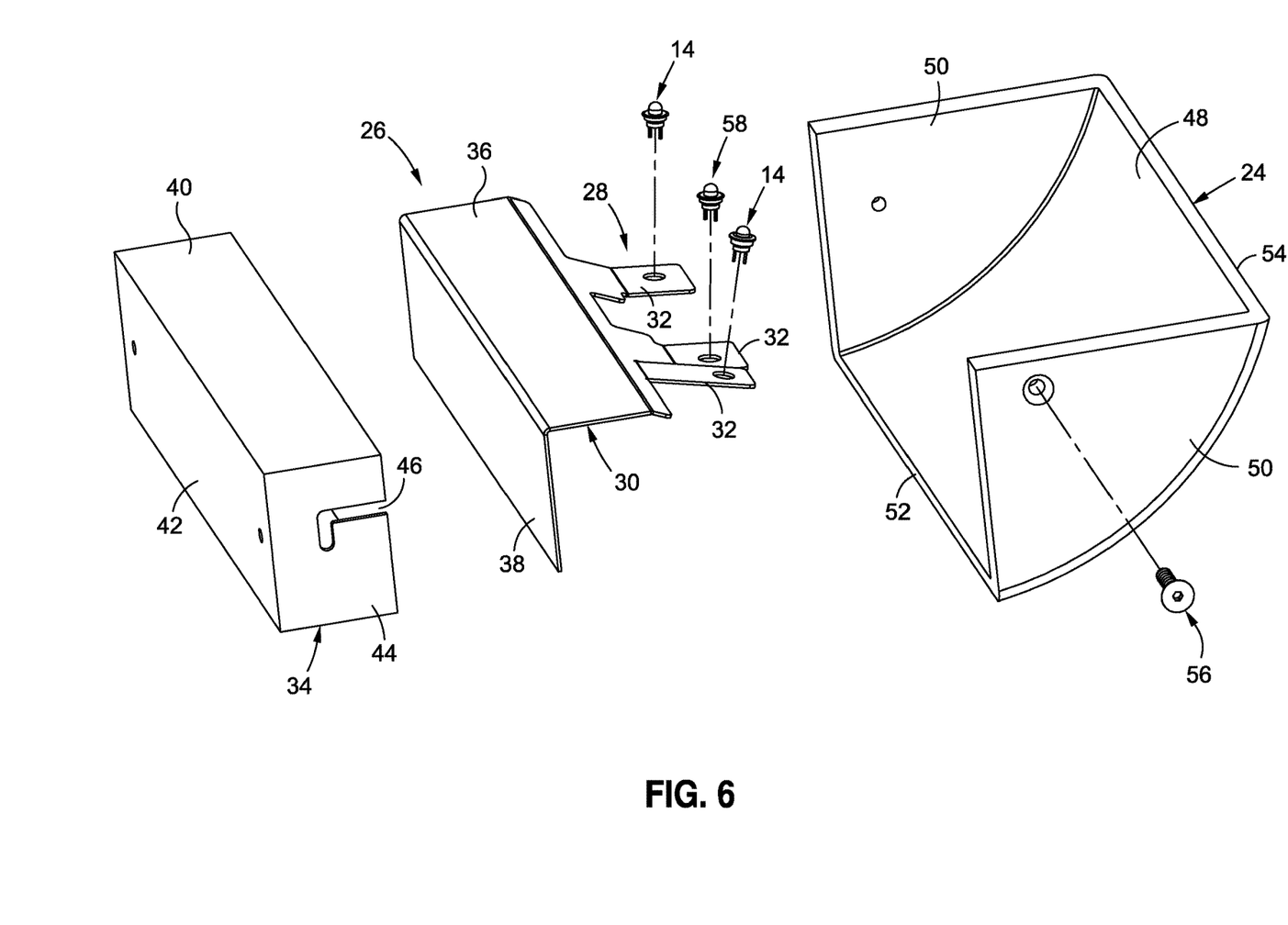
FIG. 6 is an exploded perspective view of a housing assembly.

The sanitizing light elements 14 are coupled to a chassis 26, which includes a mounting portion 28 and a bracket portion 30. The mounting portion 28 includes one or more mounting tabs 32 for engaging with respective ones of the sanitizing light elements 14. Each mounting tab 32 includes an aperture configured to receive a sanitizing light element 14. The tabs 32 extend outwardly from the bracket portion 30 to position the sanitizing light elements 14 in an optimal position for sanitizing the handle 12. To that end, the sanitizing light elements will preferably be positioned a distance one to five inches away from handle 12, whether above or below, and also will be selectively oriented a distance extending perpendicular from the door 16 such that the sanitizing light element 14 of the upper sterilization assembly 20 extends approximately one to three inches perpendicular from the door, with approximately two to three inches being most preferred and the lower sterilization assembly 22 being mounted such that the sanitizing light element 14 thereof extends a distance of at least three inches perpendicular from door 16 a distance of at least three inches, and preferably within the distance of three to five inches.

The bracket portion 30 is specifically sized and configured for connecting the chassis 26 to the shield 24. In the exemplary embodiment, the bracket portion 30 is sized and configured to be nested within a housing 34 which is connectable to the door 16. In this regard, the bracket portion 30 includes an upper bracket wall 36 and a rear bracket wall 38 that is complimentary to an upper housing wall 40 and a rear housing wall 42. When the bracket portion 30 is nested within the housing 34, the upper bracket wall 36 is positioned adjacent the upper housing wall 40, and the rear bracket wall 38 is positioned adjacent the rear housing wall 42. The housing 34 additionally includes a pair of sidewalls 44 disposed on opposed ends of the housing 34, wherein each sidewall 44 includes a slot 46 formed therein for mounting the housing 34 within the shield 24, as will be described in more detail below.

The shield 24 is positioned next to the sanitizing light elements 14 to block sanitizing light emitted away from the handle 12, and preferably to reflect light toward the handle 12. In the exemplary embodiment, the shield 24 includes an arcuate wall 48 disposed between two opposed shield end walls 50. The arcuate wall 48 extends approximately 90 degrees and includes a lower edge 52 which is positionable adjacent the door 16, and an upper edge 54 which extends away from the door 16 to define an opening therebetween through which sanitizing light may be emitted. Each shield end wall 50 includes an aperture formed therein which is sized and configured to receive a mechanical fastener 56, such as a screw, nail, rivet, etc. The mechanical fastener 56 is advanced through the respective shield end wall 50 and is configured to slide within the slot 46 formed within the housing sidewall 44 to connect the housing 34 to the shield 24.

Figure 4:
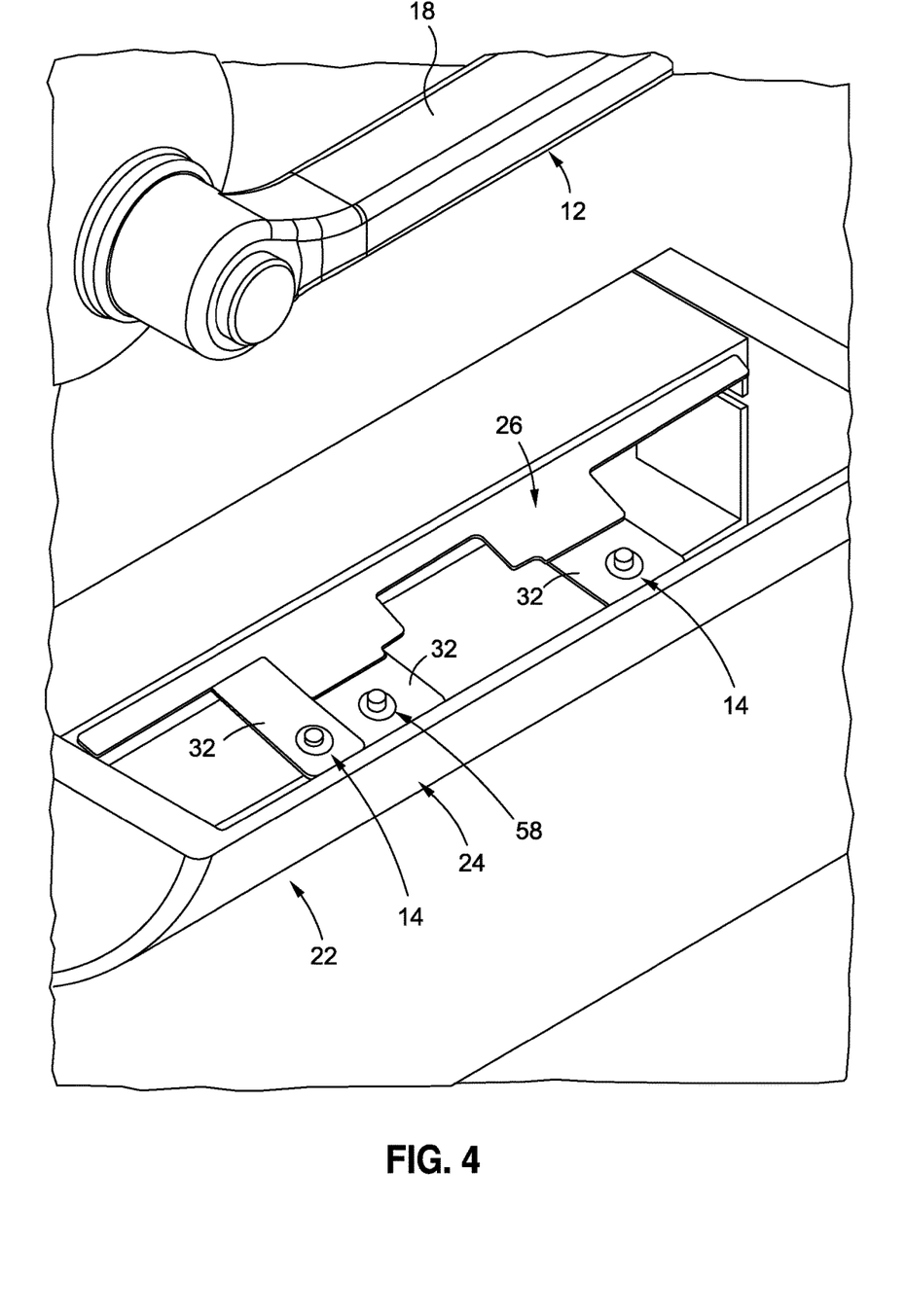
FIG. 4 is a partial, enlarged, upper perspective view of the door depicted in FIG. 1, illustrating a lower sterilization assembly.
Figure 5:
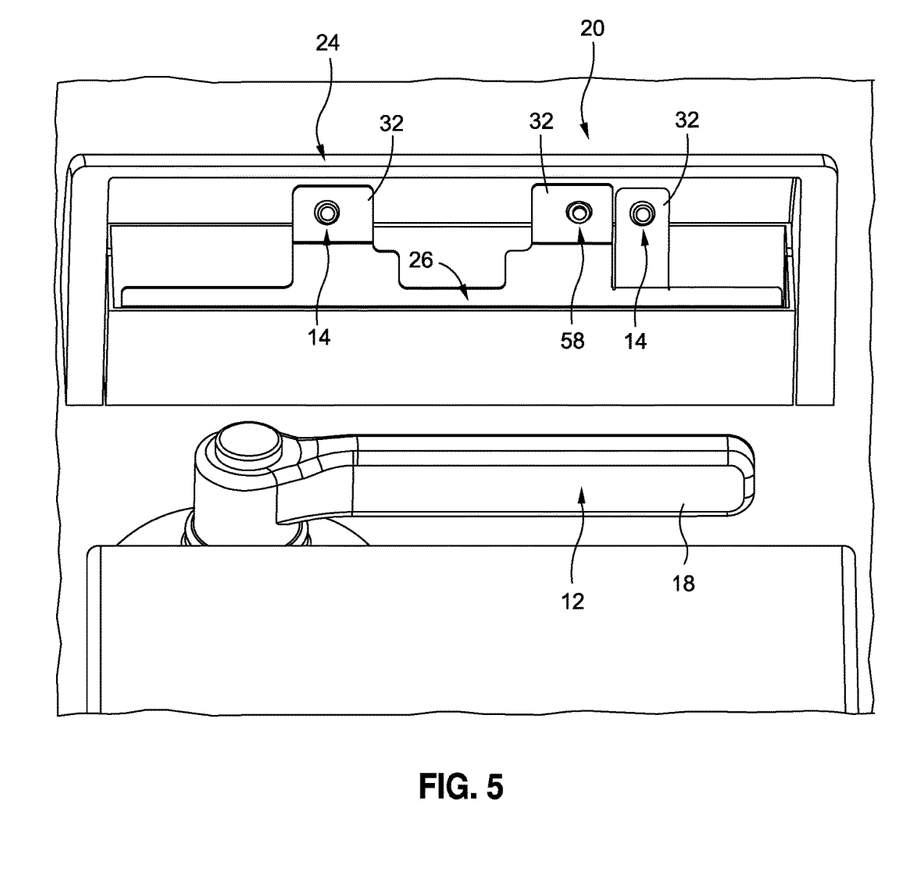
FIG. 5 is a partial, enlarged, lower perspective view of the door depicted in FIG. 1, illustrating an upper sterilization assembly.

The sterilization system 10 additionally includes a motion sensor 58 configured to detect placement and removal of a hand of a user adjacent the handle 12. The motion sensor 58 is preferably mounted to the chassis 26 on a mounting tab 32 to position the motion sensor 58 in close proximity to the handle 12. The motion sensor 58 may employ detection means known in the art, such as infrared detection, sonar detection, or the like, for detecting placement and removal of the user's hand adjacent the handle 12. When the motion sensor 58 detects the user's hand, the motion sensor 58 may generate a first detection signal, and when the motion sensor 58 detects removal of the user's hand, the motion sensor 58 generates a second detection signal. The first and second detection signals may be used to control operation of the sanitizing light elements 14, as described in more detail below.

Figure 7:
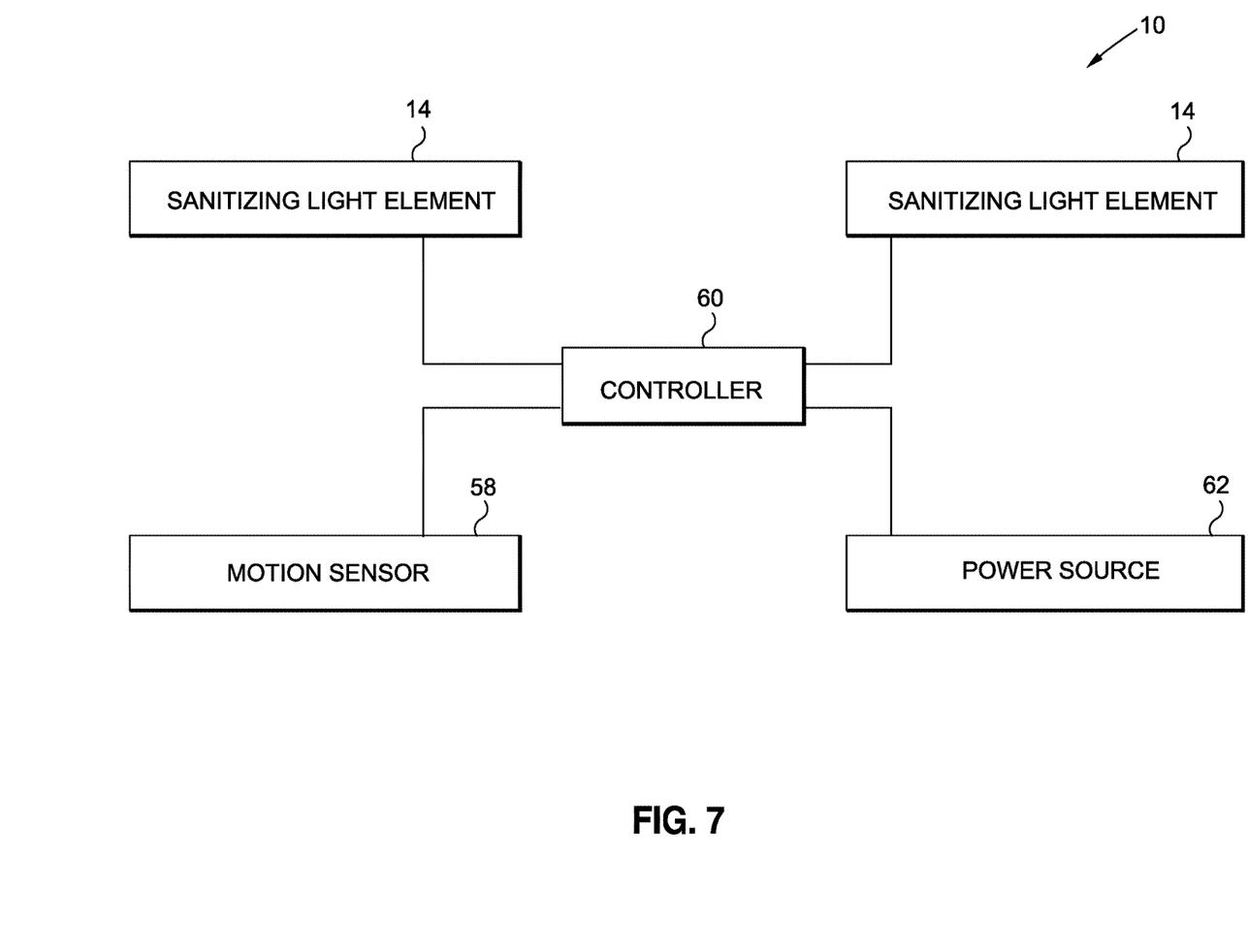
FIG. 7 is a schematic view of the electrical components according to an embodiment of the present invention.

Referring now specifically to FIG. 7, the sterilization system 10 preferably includes a controller 60 in operative communication with the motion sensor 58 and the sanitizing light element(s) 14 for controlling operation of the sterilizer(s) 14 based on information received from the motion sensor 58. According to one embodiment, the controller 60 includes the memory capacity and processing power to generate a sterilization cycle command in response to detection, by the motion sensor 58, of placement and removal of the hand of the user adjacent the handle 12. In other words, the controller 60 generates the sterilization cycle command upon receipt of the first and second detection signals.

The sanitizing light elements 14 are in communication with the controller 60 for receiving the sterilization cycle command and are adapted to emit respective optical sterilization signals toward the handle 12 for sterilizing the handle 12 in response to receipt of sterilization cycle command.

The controller 60 may be configured to generate a stop command in response to detection of placement of the hand of the user adjacent the handle 12 during emission of light by the first sanitizing light element 14. The first sanitizing light element 14 may be configured to stop emitting light in response to receipt of the stop command.

It is contemplated that the sterilization system 10 may include a local power source 62, i.e., battery, for providing power to the controller 60, motion sensor 58, and sanitizing light elements 14. Alternatively, the sterilization system 10 may receive power from an outside power source, such as a power outlet or through a hard wire connection to a building's power line.

The sterilization system 10 may be retrofitted onto existing doors 16 or walls to provide sterilization to existing handles 12, knobs, buttons, etc. Alternatively, the sterilization system 10 may be incorporated into new doors 16 or building structures during initial construction thereof.

With the primary structural elements of the sterilization system discussed above, the following will focus on operation of the sterilization system 10. Operation of the device 10 is initiated via placement of a user's hand within a detectable field adjacent the handle 12. The detectable field is defined by the motion sensor 58, which detects the user's hand as the user reaches for and grabs the handle 12. When the motion sensor 58 detects the placement of the user's hand adjacent the handle 12, the motion sensor 58 generates the first detection signal, which is then communicated to the controller 60. At this point, the controller 60 may be placed on standby to wait for removal of the user's hand. Once the motion sensor 58 detects removal of the user's hand from the detectable field, a second detection signal is generated and communicated to the controller 60.

Upon receipt of the second detection signal, the controller 60 initiates the sterilization cycle. According to one embodiment, the sterilization cycle defines a prescribed period of time which the sanitizing light elements 14 irradiate the handle 12 for sanitizing the handle 12. The controller 60 emits a sterilization cycle command to the sanitizing light elements 60, which causes the sanitizing light elements 14 to emit light at the sanitizing wavelength for the prescribed period of time. After passage of the prescribed period of time, the sanitizing light elements 60 cease the emission of light and the cycle is complete.

During the sterilization cycle, the motion sensor 58 continues to detect placement of a user's hand in close proximity to the handle 12. If the motion sensor 58 detects a user's hand during the sterilization cycle, the motion sensor 58 generates the first detection signal which is communicated to the controller 60. Furthermore, if the controller 60 receives a first detection signal during the sterilization cycle, the controller 60 generates and transmits a stop signal to the sanitizing light elements 14 to stop emitting light. Once the motion sensor 58 detects removal of the user's hand from the handle 12, and away from the detectable field, the controller 60 initiates the sterilization cycle.

When the sterilization is complete the device 10 will remain on standby mode, ready to be activated upon detection of the user's hand by the motion sensor.

According to a preferred embodiment of the invention, the device 10 sterilizes the handle of 99% of germicidal properties using the sterilization techniques described above. In this regard, the sterilization device 10 substantially maintains a sterile surface upon which a user may interact with by sterilizing the surface after each use.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A sterilization system configured for use with a door having a user actuated opening mechanism, the sterilization system comprising:
  a motion sensor configured to detect placement and removal of a hand of a user adjacent the opening mechanism;
  a controller in communication with the motion sensor, the controller being configured to generate a sterilization cycle command in response to detection by the motion sensor of placement and removal of the hand of the user adjacent the opening mechanism;
  a first sanitizing light element in communication with the controller for receiving the sterilization cycle command and positionable in optical range of the opening mechanism such that said first sanitizing light is positioned within five inches above said user actuated opening mechanism and further positioned such that said first sanitizing light extends approximately two to three inches perpendicularly outward from said door, the first sanitizing light element being sized, configured and adapted to emit a first optical sterilization signal of approximately 253.7 nm toward the opening mechanism for sterilizing the opening mechanism in response to receipt of sterilization cycle command;
  a second sanitizing light element in communication with the controller for receiving the sterilization cycle command and positionable in spaced relation to the first sanitizing light element and in optical range of the opening mechanism, the second sanitizing light element being sized, configured and adapted to emit a second optical sterilization signal toward the opening mechanism such that said second sanitizing light is positioned within five inches below said user actuated opening mechanism and further positioned such that said second sanitizing light extends approximately three to five inches perpendicularly outward from said door, the second sanitizing light element being sized, configured and adapted to emit a first second optical sterilization signal of approximately 253.7 nm, the first and second optical sterilization signals collectively sterilizing the opening mechanism in response to receipt of sterilization cycle command.

2. The sterilization system recited in claim 1 further comprising dedicated housing assemblies coupled to respective ones of said first and second sanitizing light elements, each respective assembly including a shield and a chassis coupled to the shield, each respective sanitizing light element being coupled to a respective chassis, the shield being configured to block light emitted away from the opening mechanism.

3. The sterilization system recited in claim 1, wherein the controller is configured to generate a stop command in response to detection of placement of the hand of the user adjacent the opening mechanism during emission of light by the first sanitizing light element.

4. The sterilization system recited in claim 3, wherein each respective sanitizing light element is configured to stop emitting light in response to receipt of the stop command.

5. The sterilization system recited in claim 1, wherein the motion sensor is configured to detect placement and removal of the hand of the user within approximately 5 inches of the opening mechanism.

* * * * *